(12) United States Patent
Remke et al.

(10) Patent No.: US 7,773,200 B2
(45) Date of Patent: Aug. 10, 2010

(54) METHOD AND APPARATUS FOR A SINGLE POINT SCANNER

(75) Inventors: Robert D. Remke, Chanhassen, MN (US); Todd L. Yilek, Eden Prairie, MN (US); Craig A. Benson, Maple Grove, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 265 days.

(21) Appl. No.: 11/935,922

(22) Filed: Nov. 6, 2007

(65) Prior Publication Data

US 2009/0116037 A1    May 7, 2009

(51) Int. Cl.
*G01C 3/08* (2006.01)
(52) U.S. Cl. ....................................................... 356/3.1
(58) Field of Classification Search ............. 356/3–28.5
See application file for complete search history.

(56) References Cited

U.S. PATENT DOCUMENTS 7,536,234 B2 *   5/2009   Kopelman et al. .......... 700/118
2005/0142517 A1 *   6/2005   Frysh et al. ................. 433/173

* cited by examiner

*Primary Examiner*—Thomas H Tarcza
*Assistant Examiner*—Luke D Ratcliffe
(74) *Attorney, Agent, or Firm*—Schwegman, Lundberg & Woessner, P.A.

(57) ABSTRACT

The present subject matter include methods and apparatus for creating three dimensional digitized models of at least one ear impression, the apparatus comprising a frame, a linear axis mounted to the frame, the linear axis having an axis of motion, a first spindle axis mounted to the frame, the spindle axis having an axis of rotation, wherein the axis of rotation of the first spindle axis is parallel to the axis of motion of the linear axis, a first scanner mounted to the linear axis, the scanner includes a laser for projecting a narrowly localized spot of laser light at a target mounted on the first spindle axis and a sensor array for receiving at least a portion of the laser light reflected from the target and a controller configured to communicate with the first scanner.

23 Claims, 8 Drawing Sheets

METHOD AND APPARATUS FOR A SINGLE POINT SCANNER

TECHNICAL FIELD

This application relates to digital scanning and more particularly to digital scanning to produce three dimensional digital models of ear impressions.

BACKGROUND

Many hearing assistance devices rely on at least one component residing in the ear canal of the user. A hearing assistance device user's overall satisfaction with such a device is impacted by the comfort of the device residing in the user's ear canal. Traditional methods of minimizing discomfort involve a manually intensive process of creating a hearing device housing shell from an impression of the user's ear canal. Such a process is time consuming and offers the opportunity for the introduction of errors during the manual procedures associated with the process.

SUMMARY

This document provides method and apparatus embodiments for making a detailed three dimension representation of an ear impression using a compact laser dimension sensor projecting a dot, or a narrowly localized spot, of laser light. The sensor includes both a laser source and line scan sensor within the same housing. The combination laser source and scanner, along with the sensor electronics, allow the sensor to triangulate a reflected dot or narrowly localized spot of laser beam energy generated from the sensor and projected onto the target ear impression, and determine the distance between a reference point and the point at which the laser energy is reflected from the target ear impression. Embodiments of the apparatus further include a spindle axis to rotate the surface of an ear impression within the sensing range of the sensor and a linear axis to move the sensor about one dimension of the ear impression. Additional embodiments include axes of movement to allow the sensor of the system to scan cavities and curves hidden by other structures of the impression or otherwise hidden from the two dimensional movement of the impression and the sensor. Further embodiments include the capacity to build multiple three dimensional models simultaneously such as a matching pair of models for each ear of a patient based on either one impression or a pair of impressions, one from each ear of the patient. A further embodiment of the present subject matter relates to a method of making a three dimensional model of an ear impression, including providing a first spindle, mounting a first ear impression on the first spindle, providing a first scanner for measuring the first object, calibrating the first scanner to provide a reference for measurement of the first ear impression, rotating the first spindle at a predetermined rate of rotation, positioning the first scanner at a first position to begin measurements, wherein the first position locates the scanner to measure the first ear impression near a first end of the ear impression, projecting a first narrowly localized area of laser light from the first scanner toward the first ear impression, recording a first plurality of measurements from the first scanner, processing the first plurality of measurements to generate a first three dimensional data representation of the first ear impression.

This Summary is an overview of some of the teachings of the present application and is not intended to be an exclusive or exhaustive treatment of the present subject matter. Further details about the present subject matter are found in the detailed description and the appended claims. The scope of the present invention is defined by the appended claims and their equivalents.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The subject matter of this document provide apparatus and methods for creating timely three dimensional modeling of single and complementary ear impressions, or otoplasties, for the automated manufacture of hearing assistance devices. Upon modeling the patient's ear impression, the shell of the hearing assistance device or complimentary devices can be designed. The electronic ear impression models allow efficient and flexible electronic design manipulation. Efforts to design the internal features and accommodate internal devices of the hearing assistance device become less burdensome with the use of the electronic models. Computer manipulations of the three dimensional models allow designers to develop and visually review several configurations of internal structures of the shell in a short period of time. The electronic models also allow development and visual review of the design and placement of external features such that a more comfortable and beneficial hearing assistance device is produced. Additionally, the resulting electronic models and configurations are easily duplicated, in part, so as to quickly configure a user's complimentary hearing assistance device or, to create a library of hearing assistance device characteristics that are electronically portable and selectable when configuring future devices. A machine tool, or series of machine tools, produce physical representations of the hearing assistance device using software that generates the machine tool commands from processing the electronic models originating from the scanned ear impressions. A typical machine tool is a multi-axis, computer controlled machine. A machine tool will normally control a set of tooling to remove material from a blank piece of stock or a cast or mold. Some machine tools remove the material using various bits and routers. Other machine tools use lasers to shape the object of manufacture. Some machine tool use multiple forms of tooling including bits, routers and lasers through the use of tool changers. Modeling of the user's ear begins with creating an impression of the ear canal. There are several methods of producing an ear impression that are well known in the art. The exterior contours of the resulting impression define the internal contours of a patient's ear canal. Traditionally, the impression would be used to make a mold and the mold would be used to make a shell for hearing assistance device of the patient. Such a process would normally take several weeks from the time the impression was made until a mold was produced. The subject matter of the present document provides apparatus and methods for using a single laser displacement sensor where a laser source and line scan camera are packaged in a small mountable format. In various embodiments, the Acuity AccuRange 200™ is an example of a laser displacement sensor according to the present subject matter.

Figure 1A:
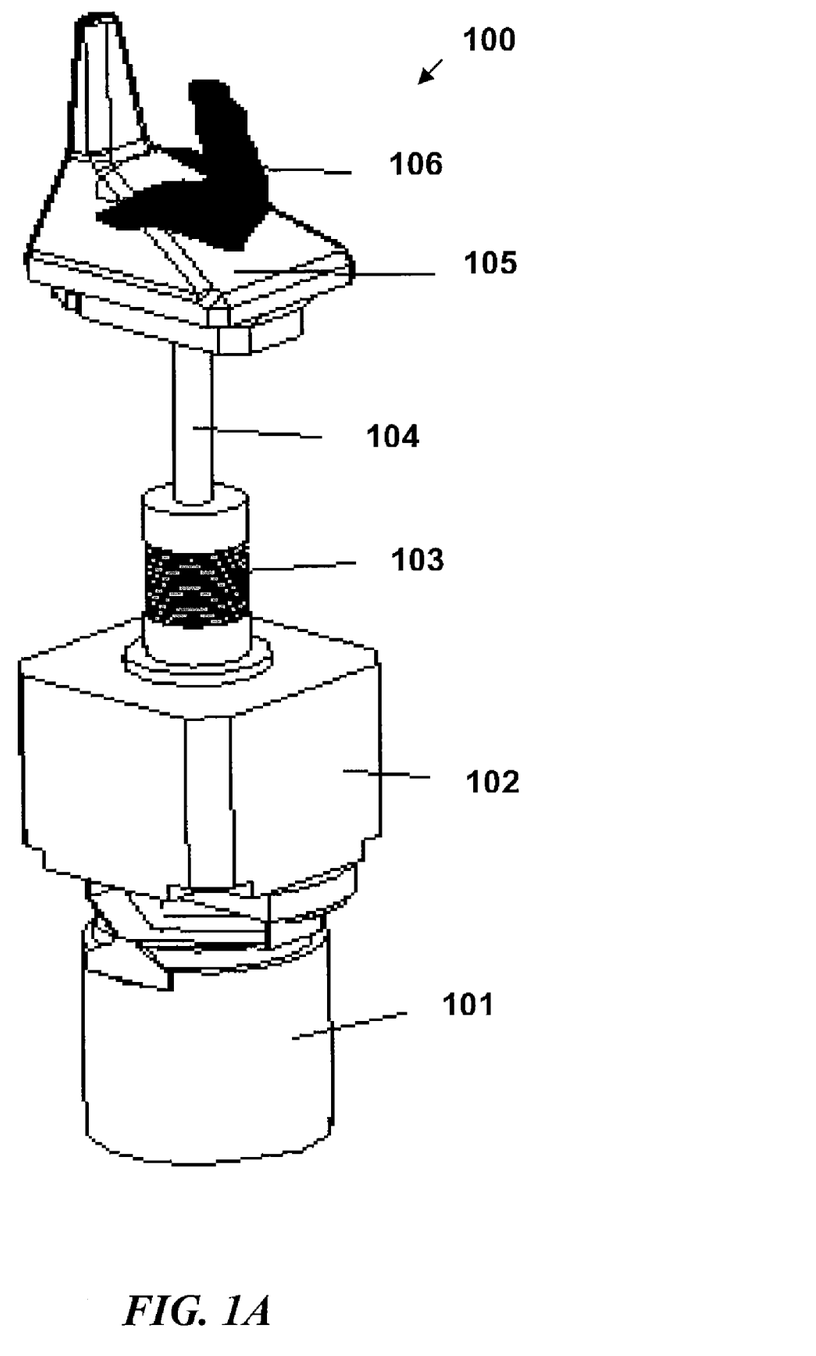
FIG. 1A illustrates one embodiment of a spindle axis according to the present subject matter.
Figure 1B:
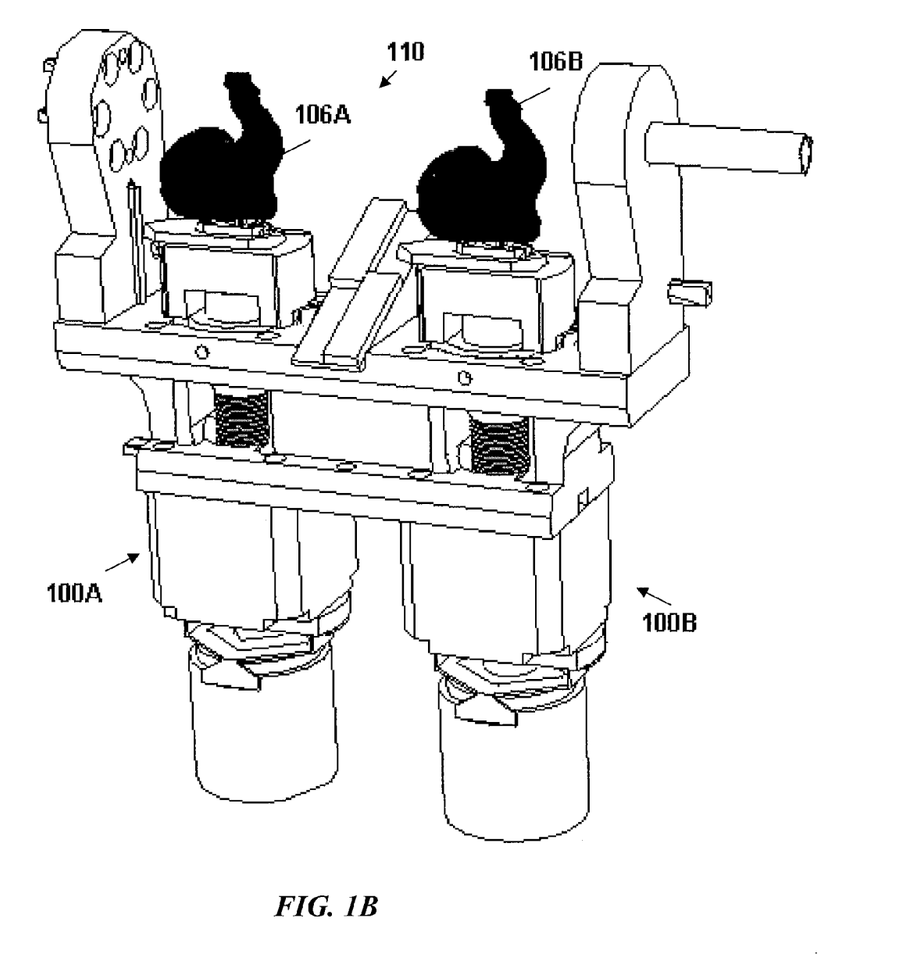
FIG. 1B illustrates two spindle axes assembled as part of a spindle pitch axis according to one embodiment of the present subject matter.

FIG. 1A illustrates one embodiment of a spindle axis 100 according to the present subject matter. The spindle axis is used to hold the ear impression and rotate it while the ear impression is scanned for modeling. The illustrate embodiment shows an encoder device 101, a motor 102, and a coupling 103 connecting the motor to the shaft 104 of the mounting device. The mounting device is hidden from view in FIG. 1A by superimposed images of a test object 105 and an ear impression 106 mounted on the spindle axis 100. FIG. 1B illustrates the two spindle axes 100A, 100B assembled as part of a spindle pitch axis 110 according to one embodiment of the present subject matter. The use of two spindles allows the simultaneous scan of a pair of ear impressions 106A, 106B. In various embodiments, the tilt axis assembly allows the axis of rotation of the spindles and, therefore, the orientation of the ear impressions to be adjusted with respect to the scanner such that difficult contours of a particular impression may be more accurately scanned. In various embodiments, the motor 102 is a servo motor. In various embodiments, the motor 102 is a stepper motor.

Figure 2:
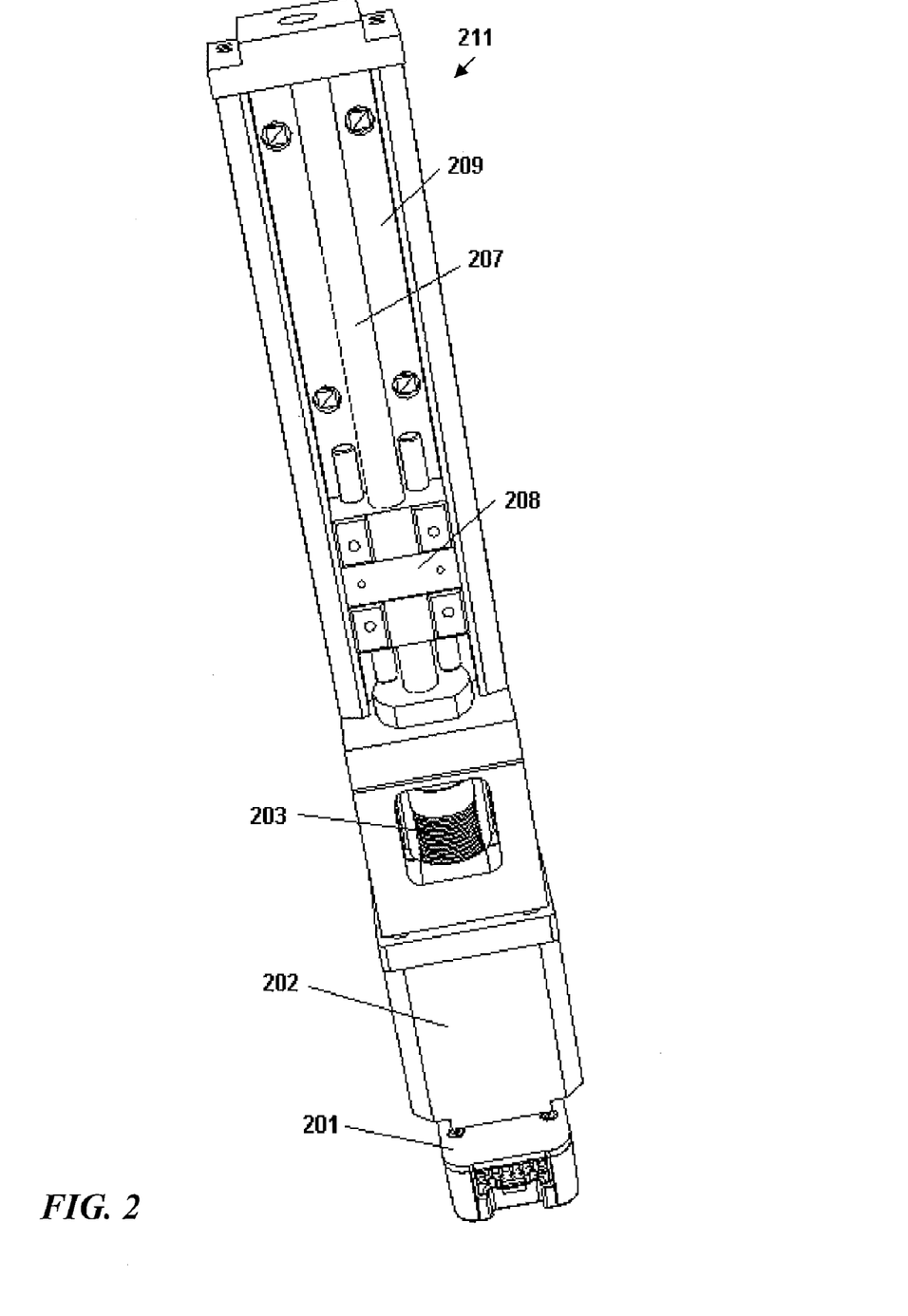
FIG. 2 illustrates a linear axis according to one embodiment of the present subject matter.

FIG. 2 illustrates a linear axis 211 according to one embodiment of the present subject matter. The linear axis supports and moves the scanner sensor used to scan the ear impression mounted on the spindle axis. The illustration shows an encoding device 201, a motor 202, a coupler 203 providing a connection between the motor 202 and a lead screw 207. FIG. 2 also shows a linear carriage 208 incorporating a nut threaded upon the lead screw 207. In addition to the lead screw 207, the carriage's linear motion and primary support is provided by a guide assembly 209. In various embodiments, bearings incorporated into the carriage 208 and the nut provide smooth and low friction motion of the carriage 208 within the guide assembly 209 and along the lead screw 207.

Figure 3:
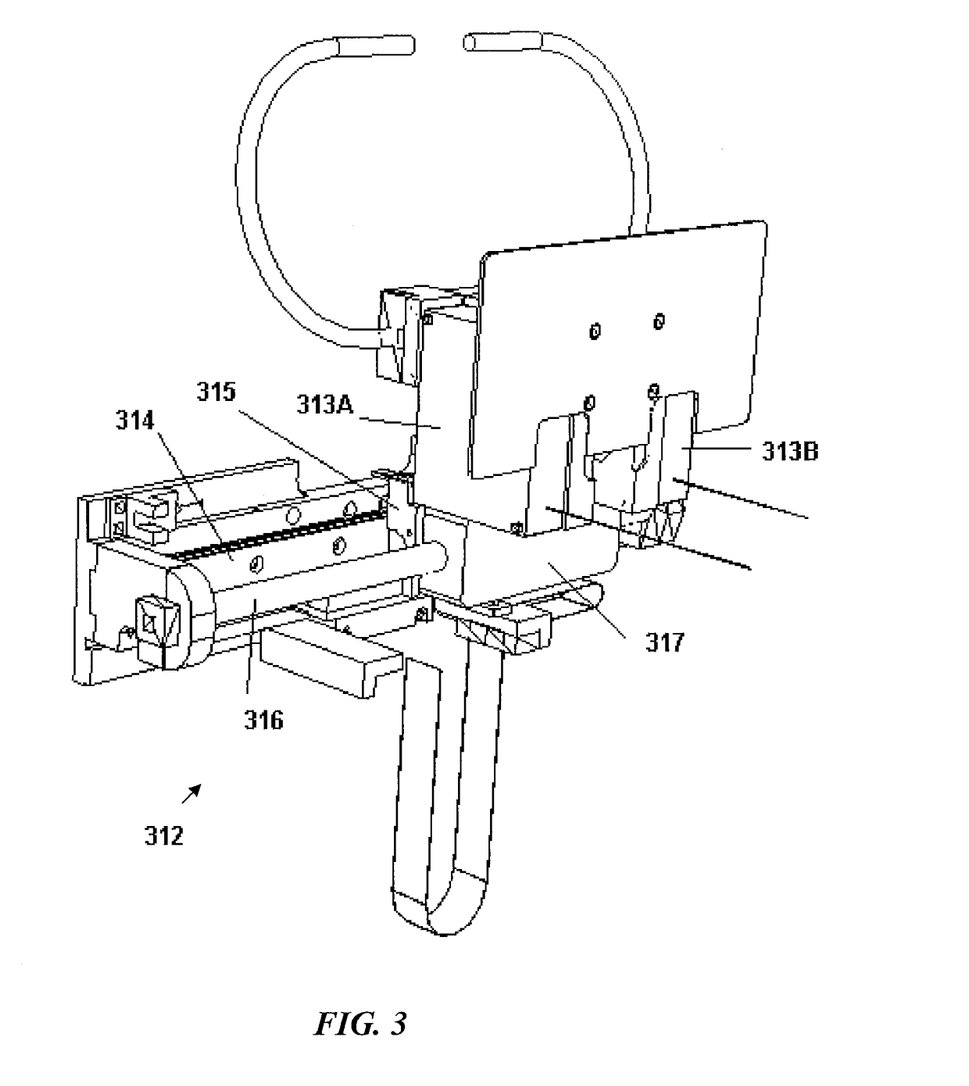
FIG. 3 illustrates a latitudinal axis assembly according to one embodiment of the present subject matter.

FIG. 3 illustrates a latitudinal axis assembly 312 according to one embodiment of the present subject matter. The latitudinal axis assembly is mounted to and moved by the linear axis (FIG. 2) according to commands of a controller. The embodiment of FIG. 3 shows two laser dimensional sensors 313A, 313B, a linear rail 314, a carriage 315 and a linear motor including a magnet tube 316 and corresponding motor winding module 317. The latitudinal axis assembly 312 allows positioning of one or more laser dimensional scanners along a path substantially perpendicular to the axis of rotation of the spindle axes and substantially perpendicular to the path of motion defined by the linear axis. When fully assembled, the laser beam of each laser dimensional sensor is directed toward an object mounted on the corresponding spindle axis as depicted in the embodiment of FIG. 6.

Figure 4:
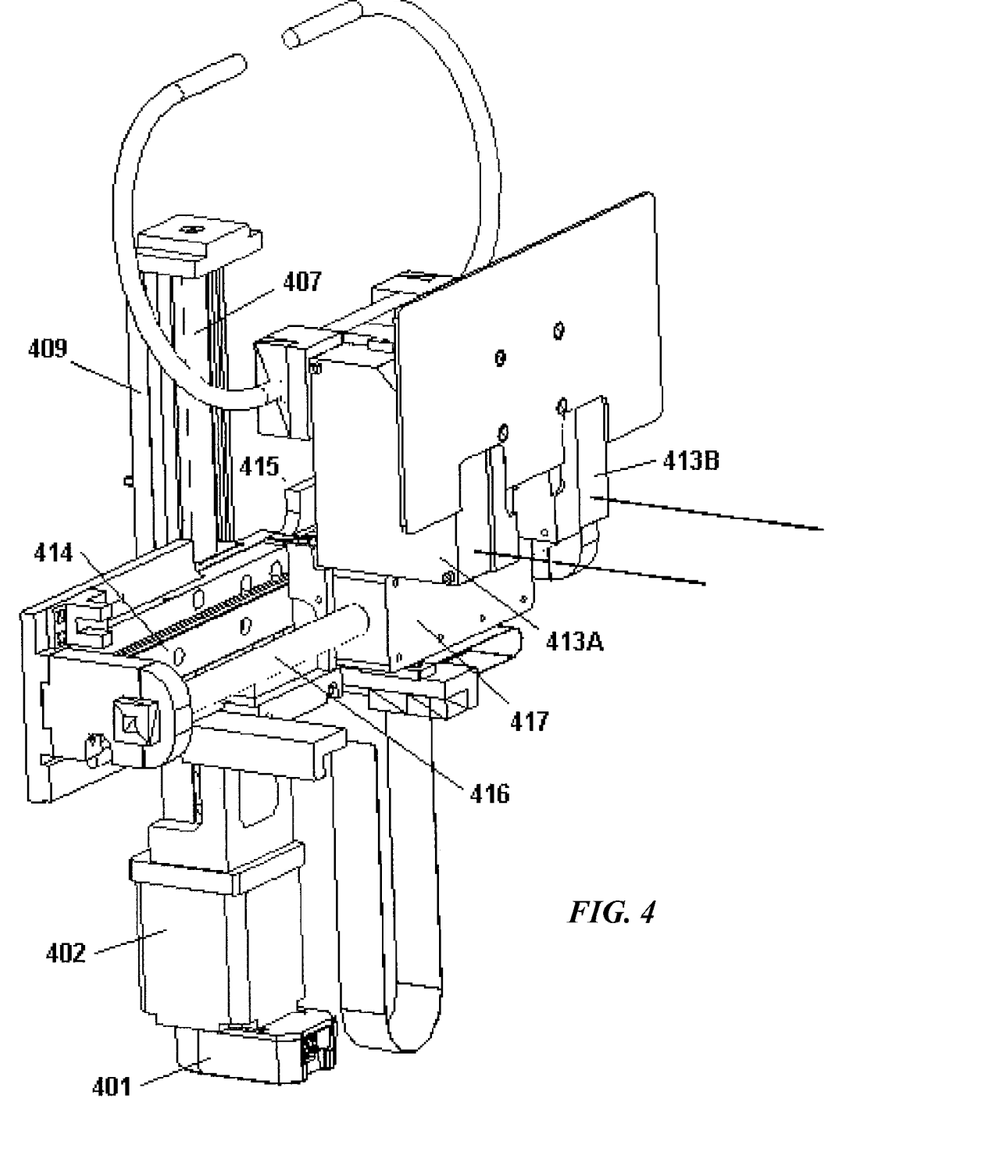
FIG. 4 illustrates a latitudinal axis assembly mounted to a linear axis according to one embodiment of the current subject matter.

FIG. 4 illustrates a latitudinal axis assembly mounted to a linear axis according to one embodiment of the current subject matter. The illustration shows an encoding device 401, a motor 402, a lead screw 407, a guide assembly 409, two laser dimensional sensors 413A, 413B, a linear rail 414, carriage 415 and a linear motor including a magnet tube 416 and corresponding motor winding module 417.

Figure 5:
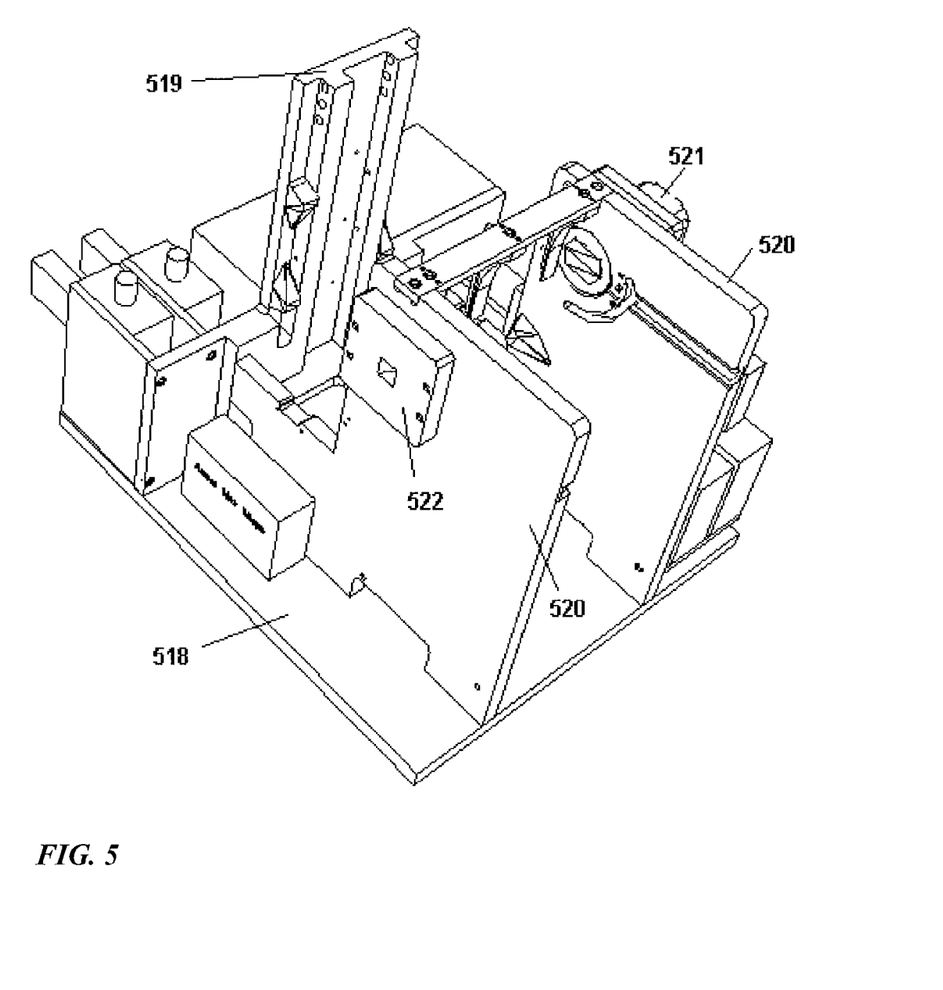
FIG. 5 illustrates a frame and assorted control components according to one embodiment of the present subject matter.

FIG. 5 illustrates a frame and assorted control components according to one embodiment of the present subject matter. The illustration includes the main base plate 518, the linear axis base plate assembly 519 and the side plates 520 for the supporting the pitch axis. With respect to the pitch axis side plates, FIG. 5 includes the pitch axis motor 521 attached to one side plate 520 and a pitch axis bearing and housing 522 attached to the other side plate 520.

Figure 6:
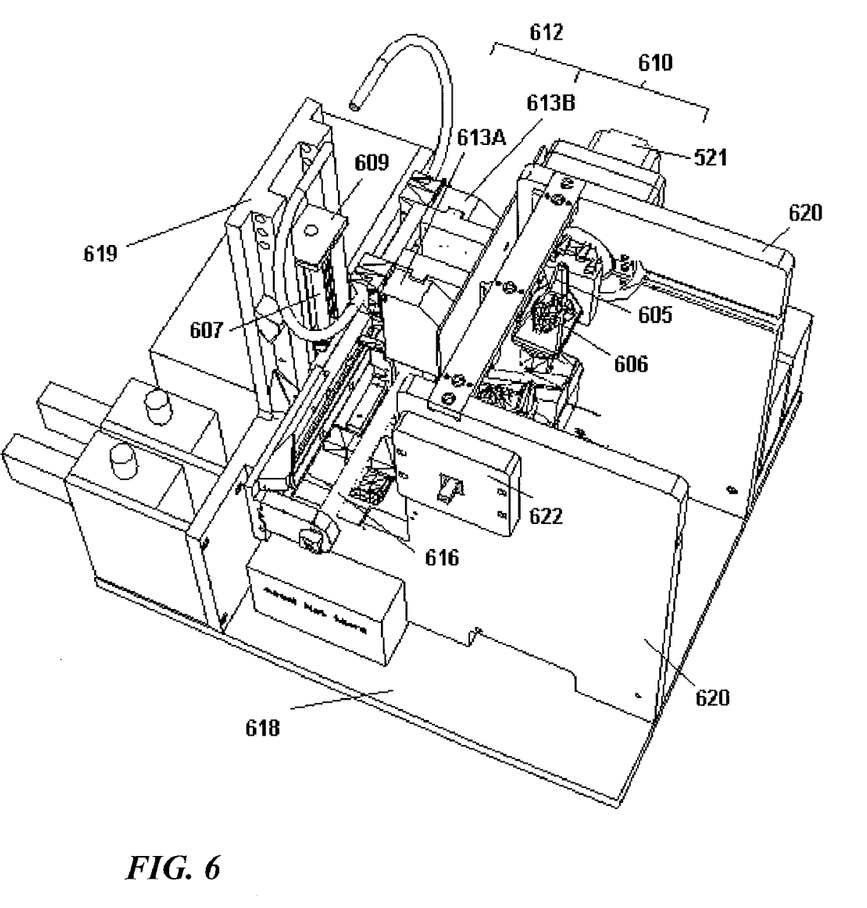
FIG. 6 illustrates an embodiment of an apparatus adapted to scan and electronically model ear impressions according to the present subject matter.

FIG. 6 illustrates an embodiment of an apparatus adapted to scan and electronically model ear impressions according to the present subject matter. The illustrated apparatus is adapted to scan and model up to two ear impressions simultaneously. The apparatus includes a main base plate 618, a pitch axis 610 with two spindle axes supported by two side plates 620, and a latitudinal axis 612 with two laser dimensional sensors 613A, 613B. In FIG. 6, an ear impression 606 and a test object 605 are shown superimposed on each other and mounted to each of the spindles. The latitudinal axis is mounted on a linear axis. The linear axis includes a linear axis guide assembly 609 and a lead screw 607. The linear axis is mounted to a linear axis base plate assembly 619.

In general, a three dimensional model of an ear impression is completed by mounting an ear impression to the apparatus and allowing the sensor to scan and the entire surface of the impression. According to the present subject matter, both the impression and the scanner are moved under the direction of a controller, such that the orientation of the impression with respect to the scanner can facilitate scanning sample points over the entire surface of the impression. A sample point is obtained by recording the position of each axis of the apparatus as well as the dimension communicated from laser dimension sensor. The laser dimension sensor measures the distance of a reflected point of laser light from a reference point associated with the sensor. The reference point is determined during calibration and is further referenced to a fixed point relative to the axes. As each dimension is communicated to the controller, the controller in turn captures the dimension of the rotary impression mount axis and the linear axis. The combined measurements allow precise determination of the position of the reflected point of laser energy within a three dimensional frame of reference.

In various embodiments, the apparatus includes a linear axis, one spindle axis and one scanner from which measurement data is collected. In such an embodiment, three measurements, one from each of the above devices, allow determination of a point, within three dimensional space, on the surface of the impression with respect to a point of reference. The accumulation of all the measurements collected in a full scan, provide a point cloud or three dimensional model of the ear impression surface. Embodiments with additional axes are capable of modeling more complex surface features of an impression such as crevices and features blocked by appendages of the impression, such as the portion of the impression corresponding to the most inner portion of an ear canal. The point cloud data is processed by at least one software application for visual display and production of a shell for a hearing assistance device housing.

Figure 7:
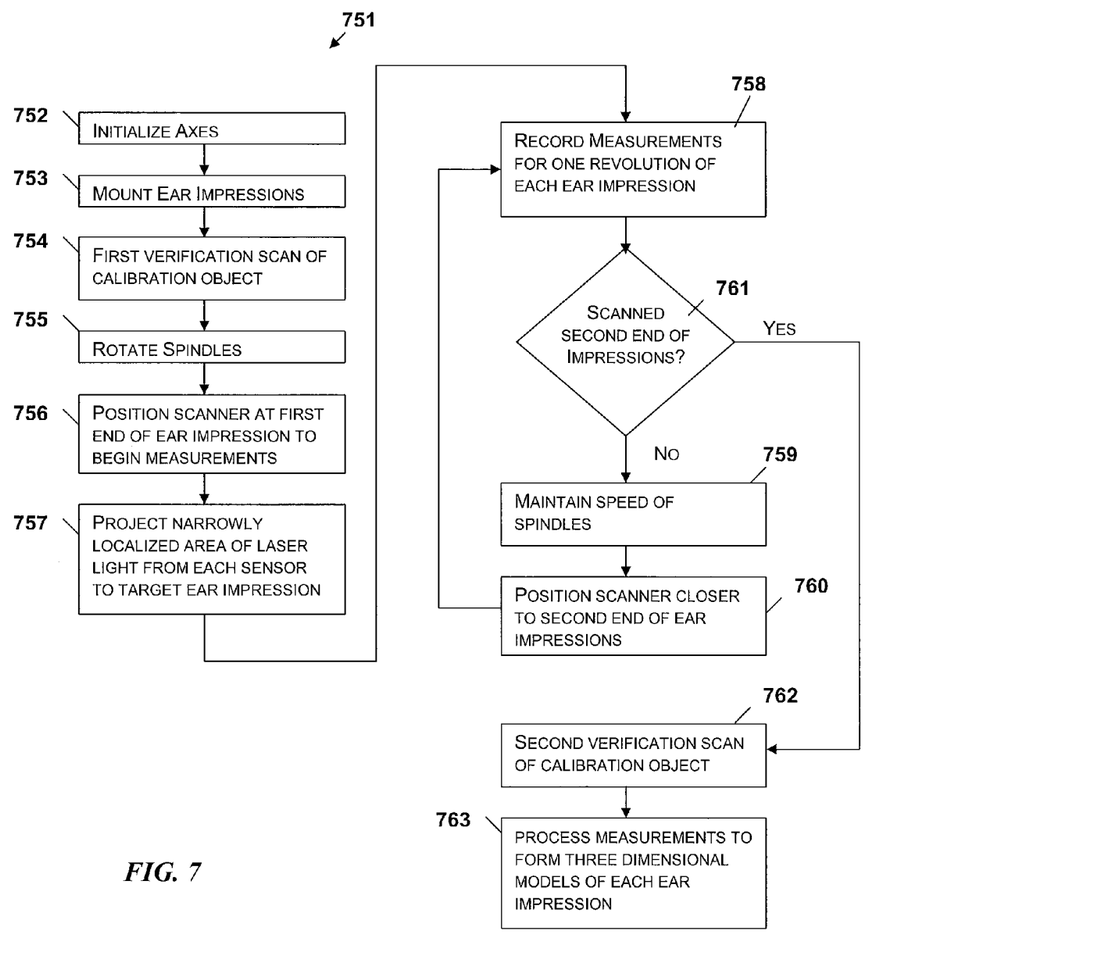
FIG. 7 illustrates one embodiment of a method 751 of generating digitized models of two ear impressions.

FIG. 7 illustrates one embodiment of a method 751 of generating digitized models of two ear impressions. Prior to scanning the first ear impression, the apparatus must be calibrated to insure that collected measurement axis data can be processed to produce accurate position data representing detected points on the surface of an ear impression mounted and moved by the rotary ear impression axis. Manufacturing of the frame and assorted mounted fixtures according to a design will provide a rough calibration provided the design dimensions are correct and have been adhered to during assembly of the apparatus.

Prior to scanning the ear impressions, initialization of the axes 752 is performed to establish a point of reference for the system, subsequent measurements and captured axis data. In various embodiments, the linear and rotary impression mount axes, or spindle axes, include incremental encoding devices to provide precise feedback of each axes' movement. Prior to initialization, the encoding devices do not provide predictable indication of the location of the axes as the initial values of the controller counters associated with each axis are typically not referenced to any reference point associated with each axis. Once initialized, the value of the axes incremental control counters provide an offset from a known reference point in a reference frame common to the entire system based on the system's prior calibration. Incremental devices do not retain reference information, therefore, initialization will need to be completed after power has been removed and re-established to either the encoder or the controller to assure an accurate model results from subsequently scanned ear impressions.

In various embodiments, an axis uses an absolute encoder. Embodiments with an absolute encoder and corresponding controls, including absolute encoding devices such as an absolute resolver or absolute encoder. Initialization is required only after an absolute encoding device is initially installed onto the axis. In embodiments with absolute encoding devices, the operation of the absolute encoding device allows automatic initialization of an axis without movement of the axis, even after power is removed and re-established from the device or the control.

In the illustrated method, the ear impressions are mounted to the spindle axes 753 after the axes are initialized. In various embodiments, the ear impressions are mounted to the spindle axes prior to the initialization of the axes.

In various embodiments, after initialization of the axes, calibration may be verified 754 and, if needed, adjusted to compensate for changes, for example, from wear of bearings and dimensional changes resulting from the environment, such as temperature. In various embodiments, verification includes mounting an object of known dimension on each spindle axis and scanning a model of the object. The scanned model is then compared to the model's verified dimensions. Calibration parameters of the system are adjusted such that the scanned model fits the model of the verified object. In various embodiments, the verification process includes scanning verified objects specially made such that each axis or device, such as the laser dimension sensor, may be verified individually over the full range of each axes' motion. This type of verification allows precise calibration, for example, of the straightness of the linear axis over that axis' full travel, the radial play of the spindle bearings, as well as, the alignment of the linear axis with the axis of rotation of the spindles. If the verification process can not rectify the calibration of these or other calibration parameters, the system raises an alert such that inspection and physical adjustment of the system can be performed. The verification measurements will be used with a second, future set of measurements to assist in deriving the final point cloud of each ear impression.

After the system is verified, a scan of an ear impression begins. The controller triggers the spindle axes to accelerate and begin rotating at a predetermined and constant speed 755. In various embodiments, when the rotary axes reach a steady state speed at or near the predetermined speed, the controller triggers the laser dimension sensors to communicate measurement data. The data is communicated to the controller at a rate of up to 1250 measurements per second using various communication protocols and hardware. In various embodiments, the communication uses a serial network, such as RS232 or RS422. Other communication formats may also be used, for example, a direct analog input, Ethernet, ControlNet, DeviceNet, or ProfiBus. In various embodiments, the recording of measurements includes simultaneously capturing the positions of both the linear axis and the rotary impression mount axes. The measurement and positions are recorded for future processing.

The actual scan of the ear impressions begin with positioning each axis such that the narrowly localized area of laser light from each sensor 757 is directed at the ear impression, usually at or near one extreme of the impression with respect to the linear axis 756.

In various embodiments, after measurements have been recorded for at least one revolution of each impression 758, the controller moves the linear axis incrementally toward the other extreme of the impression 760, stops the linear axis, and records measurements and positions for another rotation of the impression. This pattern of, measure for a rotation of each impression, move linear axis and repeat, continues until the entire impression is scanned 761. The rotational speed of the spindle axes is maintained throughout the scanning process 759. In one embodiment of the present subject matter, the controller begins a continuous movement of the linear axis toward the other extreme of the impression after the initial scan of the first revolution of the impression is complete. As the linear axis travels toward the other extreme of the impression. the controller continuously captures measured data and corresponding position information until the entire impression is scanned. Once the actual scan of the ear impression is complete, the system makes a second scan of the calibration device 762 for use in deriving the point cloud and correcting for rotational orientation errors in the collected data.

In various embodiments, the system collects two arrays of data throughout the scanning process. The data arrays include an array of position measurements and corresponding timestamps of the measurements, and an array of laser measurements and corresponding timestamps of the laser measurements. In various embodiments, a scanner communicates 1250 measurements per second. Using such a scanner, a 14,000 point "point cloud" is derived from as many as 75,000 measurements collected in each of the arrays. Upon derivation of the point cloud, a surface is electronically fitted to the point cloud and is built into a electronically storable Stereolithography Tessellation Language (STL) computer file 763. In various embodiments, the measurements, derivation and surface fitting is completed in less than 180 seconds. In various embodiments, the finished model is accurate to within 0.001 inch of the actual impression.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. An apparatus for creating three dimensional digitized models of one or more ear impressions, the apparatus comprising:
   a frame;
   a linear axis mounted to the frame, the linear axis having an axis of motion;
   a first spindle axis mounted to the frame, the first spindle axis having a first axis of rotation, wherein the first axis of rotation is parallel to the axis of motion of the linear axis;
   a second spindle axis mounted to the frame, the second spindle axis having a second axis of rotation, wherein the second axis of rotation is parallel to the axis of motion of the linear axis;
   a first scanner mounted to the linear axis, the scanner adapted to project a first narrowly localized spot of laser light toward the first spindle axis;
   a second scanner mounted to the linear axis, the second scanner adapted to project a second narrowly localized spot of laser light toward the second spindle axis;
   a controller adapted to communicate with the first and second scanners;
   a latitudinal axis mounted between the linear axis and the first and second scanners, the latitudinal axis having an axis of motion perpendicular to the travel of the linear axis; and
   a pitch axis mounted to the frame, wherein the first spindle axis is mounted to the pitch axis and the pitch axis has an axis of rotation perpendicular to the travel of the linear axis and parallel to the axis of motion of the latitudinal axis.

2. The apparatus of claim 1, wherein the second spindle axis is mounted to the frame using the pitch axis.

3. The apparatus of claim 1, wherein the first spindle axis includes a first calibration disk configured to be scanned using the first scanner 4. The apparatus of claim 1, wherein the second spindle axis includes a second calibration disk configured to be scanned using the second scanner 5. The apparatus of claim 1, wherein the first scanner is configured to sense and communicate to the controller a first dimension representative of the distance between a detected surface of a first ear impression mounted to the first spindle and a predetermined reference point associated with the position of the first scanner.

6. An apparatus for creating three dimensional digitized models of one or more ear impressions, the apparatus comprising:
   a frame;
   a linear axis mounted to the frame, the linear axis having an axis of motion;
   a first spindle axis mounted to the frame, the first spindle axis having a first axis of rotation, wherein the first axis of rotation is parallel to the axis of motion of the linear axis;
   a second spindle axis mounted to the frame, the second spindle axis having a second axis of rotation, wherein the second axis of rotation is parallel to the axis of motion of the linear axis;
   a first scanner mounted to the linear axis, the scanner adapted to project a first narrowly localized spot of laser light toward the first spindle axis;
   a second scanner mounted to the linear axis, the second scanner adapted to project a second narrowly localized spot of laser light toward the second spindle axis; and
   a controller adapted to communicate with the first and second scanners,
   wherein the first scanner is configured to sense and communicate to the controller a first dimension representative of the distance between a detected surface of a first ear impression mounted to the first spindle and a predetermined reference point associated with the position of the first scanner 7. The apparatus of claim 6, further comprising a latitudinal axis mounted between the linear axis and the first and second scanners, the latitudinal axis having an axis of motion perpendicular to the travel of the linear axis.

8. An apparatus comprising:
   a first laser displacement sensor having a predetermined sensing range, wherein the first laser displacement sensor is configured to project a first narrowly localized spot of laser light, detect reflected laser light from the first narrowly localized spot of laser light and determine a first distance from a first predetermined reference point and a point of reflection of the first narrowly localized spot of laser light within the predetermined sensing range of the first laser displacement sensor;
   a first spindle axis having an axis of rotation and configured to rotate a first ear impression coupled to the first spindle within the predetermined sensing range of the first laser displacement sensor;
   a pitch axis coupled to the first spindle axis, the pitch axis having an axis of rotation perpendicular to the axis of rotation of the first spindle axis and configured to rotate the first spindle axis about the axis of rotation of the pitch axis; and
   a controller configured to record measurement data from the first laser displacement sensor and rotational position data of the first spindle axis.

9. The apparatus of claim 8, wherein the pitch axis includes a pitch axis motor to rotate the pitch axis.

10. The apparatus of claim 9, wherein the pitch axis motor is a servo motor.

11. The apparatus of claim 9 wherein the pitch axis motor is a stepper motor.

12. The apparatus of claim 8, further comprising a linear axis connected to the first laser displacement sensor and configured to move the first laser displacement sensor along a path parallel to the axis of rotation of the first spindle axis.

13. The apparatus of claim 12, wherein the linear axis includes a servo motor.

14. The apparatus of claim 12, further comprising a latitudinal axis connected between the linear axis and the first laser displacement sensor and configured to move the first laser displacement sensor along an axis perpendicular to the axis of rotation of the first spindle axis.

15. The apparatus of claim 14, wherein the latitudinal axis includes a latitudinal axis motor.

16. The apparatus of claim 15, wherein the latitudinal axis motor includes a latitudinal axis servo motor.

17. The apparatus of claim 16, wherein the latitudinal axis motor is a linear servo motor.

18. The apparatus of claim 14, further comprising:
   a second laser displacement sensor mounted to the latitudinal axis, the second laser displacement sensor having a predetermined sensing range, wherein the second laser displacement sensor is configured to project a second narrowly localized spot of laser light, detect reflected laser light from the second narrowly localized spot of laser light and determine a second distance from a second predetermined reference point and a point of reflection of the second narrowly localized spot of laser light in the predetermined sensing range of the second laser displacement sensor; and a second spindle axis having an axis of rotation and configured to rotate a second ear impression coupled to the second spindle axis within the predetermined sensing range of the second laser displacement sensor.

19. A method for creating digitized models of ear impressions, the method comprising:

providing a first spindle;
mounting a first ear impression on the first spindle;
providing a first scanner for measuring the first object;
calibrating the first scanner to provide a reference for measurement of the first ear impression;
rotating the first spindle at a predetermined rate of rotation;
positioning the first scanner at a first position to begin measurements, wherein the first position locates the scanner to measure the first ear impression near a first end of the ear impression;
projecting a first narrowly localized spot of laser light from the first scanner upon the first ear impression;
recording a first plurality of measurements from the first scanner; and
processing the first plurality of measurements to generate a first three dimensional data representation of the first ear impression, wherein recording a first plurality of measurements includes simultaneously recording the first plurality of measurements and rotating the first spindle at the predetermined speed.

20. The method of claim 19, further comprising:
providing a second spindle;
mounting a second ear impression on the second spindle;
providing a second scanner for measuring the second ear impression;
calibrating the second scanner to provide a reference for measurement of the second ear impression;
rotating the second spindle at the predetermined rate of rotation;
positioning the second scanner at a second position to begin measurements;
projecting a second narrowly localized area of laser light from the second scanner toward the second ear impression;
simultaneously recording a second plurality of measurements from the second scanner and rotating the second spindle axis at the predetermined rate of rotation; and
processing the second plurality of measurements to generate a second three dimensional data representation of the second ear impression.

21. The method of claim 19, wherein recording a first plurality of measurements from the first scanner includes:
positioning the first scanner along a path parallel to the axis of rotation of the first spindle and closer to a second end of the first ear impression opposite the first end of the ear impression;
recording a portion of the first plurality of measurements for at least one rotation of the first spindle; and
repeating the positioning of the first scanner closer to the second end of the first ear impression and recording a portion of the first plurality of measurements for at least one rotation of the first spindle at each of the first scanner positions.

22. The method of claim 20, further comprising:
storing the first digitized three dimensional representation of the first ear impression in a first electronically storable Stereolithography Tessellation Language (STL) computer file; and
storing the second digitized three dimensional representation of the second ear impression in a second electronically storable STL computer file.

23. The method of claim 22, further comprising:
providing instructions and tool path commands for computer aided manufacturing of a first hearing assistance device housing using the first electronically storable STL computer file;
and providing instructions and tool path commands for computer aided manufacturing of a second hearing assistance device housing using the second electronically storable STL computer file.

* * * * *